United States Patent
Zard et al.

(10) Patent No.: US 8,871,975 B2
(45) Date of Patent: Oct. 28, 2014

(54) PROCESS FOR THE SYNTHESIS OF AGOMELATINE

(75) Inventors: Samir Zard, Gif-sur-Yvette (FR); Béatrice Sire, Palaiseau (FR); Mehdi Boumediene, Choisy le Roi (FR)

(73) Assignee: Les Laboratories Servier, Suresnes Cedex (FR)

( * ) Notice: Subject to any disclaimer, the term of this patent is extended or adjusted under 35 U.S.C. 154(b) by 0 days.

(21) Appl. No.: 13/977,796

(22) PCT Filed: Jan. 4, 2012

(86) PCT No.: PCT/FR2012/000004
§ 371 (c)(1),
(2), (4) Date: Jul. 1, 2013

(87) PCT Pub. No.: WO2012/093225
PCT Pub. Date: Jul. 12, 2012

(65) Prior Publication Data
US 2013/0289308 A1    Oct. 31, 2013

(30) Foreign Application Priority Data
Jan. 5, 2011  (FR) .................................... 11 00023

(51) Int. Cl.
*C07C 233/05*  (2006.01)
*C07C 231/12*  (2006.01)
*C07C 231/14*  (2006.01)
*C07C 231/10*  (2006.01)
*C07D 209/48*  (2006.01)

(52) U.S. Cl.
CPC .............. *C07C 231/14* (2013.01); *C07C 231/10* (2013.01); *C07D 209/48* (2013.01); *C07C 2102/10* (2013.01); *C07C 231/12* (2013.01)

USPC ........................................... 564/219; 560/170

(58) Field of Classification Search
USPC ........................................... 564/219; 560/170
See application file for complete search history.

(56) References Cited

U.S. PATENT DOCUMENTS

| 5,318,994 | A  | 6/1994 | Andrieux et al. |
| 7,544,839 | B2 | 6/2009 | Souvie et al. |
| 8,212,077 | B2 | 7/2012 | Hardouin et al. |

FOREIGN PATENT DOCUMENTS

| EP | 0447285 | 9/1991 |
| EP | 1564202 | 8/2005 |
| EP | 2151428 | 2/2010 |

OTHER PUBLICATIONS

E. Fourmaintraux. et al., Bioorganic & Medicinal Chemistry, vol. 6, No. 1, p. 9-13, 1998.
International search report for PCT/FR2012/000004 of Mar. 16, 2012.

*Primary Examiner* — Shailendra Kumar
(74) *Attorney, Agent, or Firm* — Hueschen and Sage

(57) ABSTRACT

Process for the industrial synthesis of the compound of formula (I)

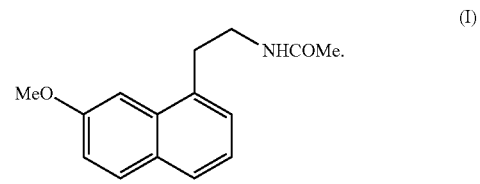

27 Claims, No Drawings

PROCESS FOR THE SYNTHESIS OF AGOMELATINE

The present invention relates to a new process for the industrial synthesis of agomelatine, or N-[2-(7-methoxy-1-naphthyl)ethyl]acetamide, of formula (I):

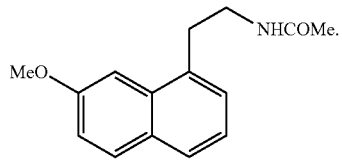
(I)

Agomelatine, or N-[2-(7-methoxy-1-naphthyl)ethyl]acetamide, has valuable pharmacological properties.

It has, in fact, the double characteristic of being, on the one hand, an agonist of receptors of the melatoninergic system and, on the other hand, an antagonist of the 5-HT$_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European patent specifications EP 0 447 285 and EP 1 564 202.

In view of the pharmaceutical value of this compound, it has been important to be able to produce it using an effective industrial synthesis process which is readily transferable to the industrial scale and which provides agomelatine in a good yield and with excellent purity.

Patent specification EP 0 447 285 describes production of agomelatine in eight steps starting from 7-methoxy-1-tetralone.

In patent specification EP 1 564 202, the Applicant developed a new, much more effective and industrialisable synthesis route in only four steps starting from 7-methoxy-1-tetralone that makes it possible to obtain agomelatine in highly reproducible manner in a well-defined crystalline form.

However, the search for new synthesis routes, especially starting from starting materials that are less costly than 7-methoxy-1-tetralone, is currently still relevant.

The Applicant has continued his investigations and has developed a new process for the synthesis of agomelatine starting from 1-(4-methoxyphenyl)-4-penten-1-one and a xanthate compound: these new starting materials have the advantage of being simple and readily obtainable in large quantities at less cost.

This synthesis route is based on the performance of free radical reactions that are not very commonly used but are nevertheless very effective. Converting these reactions to the industrial scale using continuous-flow reactors is promising as it becomes simpler to control propagation of the chain reaction.

This new process moreover makes it possible to obtain agomelatine in reproducible manner and without requiring laborious purification, with a purity that is compatible with its use as a pharmaceutical active ingredient. Indeed, agomelatine can accordingly be synthesised in 6 steps in the course of which only one of the intermediates is isolated.

More specifically, the present invention relates to a process for the industrial synthesis of the compound of formula (I):

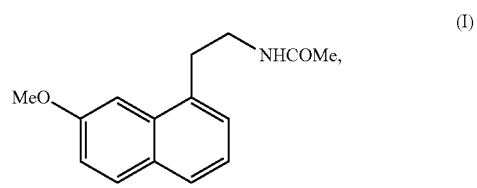
(I)

which process is characterised in that 1-(4-methoxyphenyl)-4-penten-1-one of formula (II):

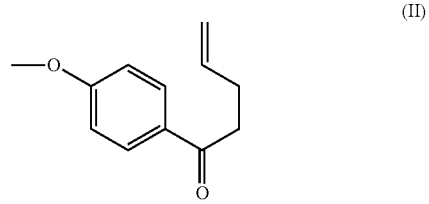
(II)

is reacted, in the presence of a free radical initiator with a compound of formula (III):

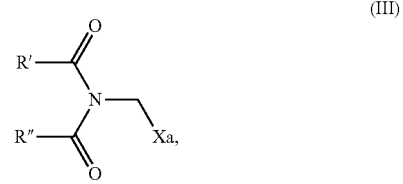
(III)

wherein R' and R", which may be the same or different, each represent a linear or branched (C$_1$-C$_6$)alkyl group or R' and R" together form a (C$_2$-C$_3$)alkylene chain, it being possible for the ring thereby formed to be fused with a phenyl group, and Xa represents a group —S—C(S)—OR in which R represents a linear or branched (C$_1$-C$_6$)alkyl group, to yield the adduct of formula (IV):

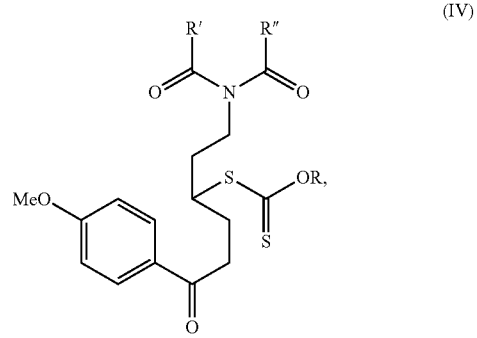
(IV)

wherein R, R' and R" are as defined hereinbefore,
it being possible for the compound of formula (IV) optionally to be isolated,
the amine function of which may optionally be deprotected and converted into an acetamide function,
which is subjected to a cyclisation reaction in the presence of a free radical initiator to form the compound of formula (V):

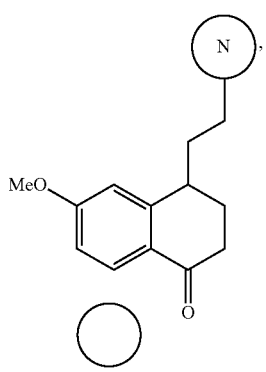 (V)

it being understood that the group —N denotes a protected amine function defined as follows:

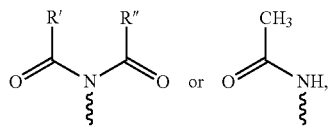

wherein R' and R" are as defined hereinbefore, the amine function of which compound of formula (V) may optionally be deprotected, said compound of formula (V) is either subjected to reduction-esterification followed by dehydration or converted into a vinyl halide to yield the compound of formula (VI):

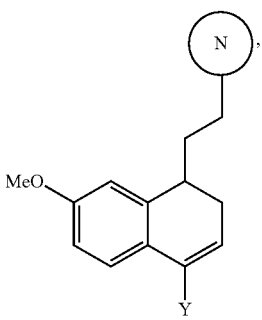 (VI)

wherein Y represents a halogen atom (referred to as X hereinbelow) or a hydrogen atom, the

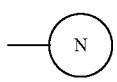

group being as defined hereinbefore, the protected amine function of which compound of formula (VI) is converted into an acetamide function where applicable, i.e. when that conversion has not been carried out earlier, to yield the compound of formula (VI'):

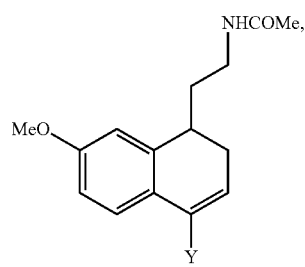 (VI')

wherein Y is as defined hereinbefore, which is finally subjected to an aromatisation reaction to yield the compound of formula (I), which is isolated in the form of a solid.

The compound of formula (II) is accessible to the person skilled in the art by means of conventional chemical reactions and/or chemical reactions described in the literature (Pattisson, V. A. et al., *J. Am. Chem. Soc.* 1962, 84, 4295).

Preferred compounds of formula (III) are:

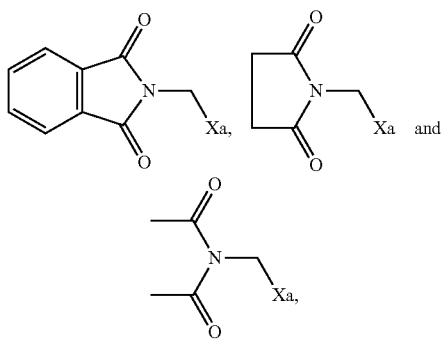

wherein Xa=-S—C(S)—OR is as defined hereinbefore.

In a preferred Xa group, R represents an ethyl group.

In the processes according to the invention, initiation of the free radical reactions is carried out by thermal means. Preferably, the reaction mixture is heated to a temperature of from 50° C. to 140° C.

Peroxides are free radical initiators that are especially suitable for carrying out the step of addition of the compound of formula (II) to the compound of formula (III), or for performing cyclisation of the compound of formula (IV) to form the compound of formula (V). By way of example, there may be mentioned, especially, diisobutyryl peroxide, cumyl peroxyneodecanoate, tert-amyl peroxyneodecanoate, di(2-ethylhexyl) peroxydicarbonate, tert-butyl peroxyneodecanoate, dibutyl peroxydicarbonate, dicetyl peroxydicarbonate, dimyristyl peroxydicarbonate, tert-butyl peroxyneoheptanoate, tert-amyl peroxypivalate, didecanoyl peroxide, tert-amyl peroxy-2-ethylhexanoate, tert-butyl peroxyisobutyrate, 1,4-di(tert-butylperoxycarbo)cyclohexane, tert-butyl peroxyacetate, tert-butyl peroxybenzoate, di-tert-amyl peroxide, tert-butyl cumyl peroxide, bis(tert-butyl) peroxide, dicumyl peroxide, dilauroyl peroxide (DLP), dibenzoyl peroxide or di(4-tert-butylcyclohexyl) peroxydicarbonate.

Preferably, the addition reaction is initiated in the presence of dilauroyl peroxide.

In a preferred embodiment of the invention, the reaction of cyclisation of the adduct of formula (IV) is carried out in the presence of dilauroyl peroxide optionally with dibenzoyl peroxide.

The addition and/or cyclisation reactions are carried out in a solvent customarily used in free radical chemistry such as 1,2-dichloroethane, dichloromethane, benzene, toluene, trifluoromethylbenzene, chlorobenzene, hexane, cyclohexane, heptane, octane, ethyl acetate, tert-butyl alcohol, and mixtures thereof.

Preference is given to using ethyl acetate in the processes according to the invention.

When the amine function of the compound of formula (V) is protected by a phthalimide group (i.e. R' and R" together form an ethylene chain, the ring thereby formed being fused to a phenyl group):

the compound of formula (V) is advantageously subjected to an amine-deprotecting reaction and then reacted with acetic anhydride to form the compound of formula (VII):

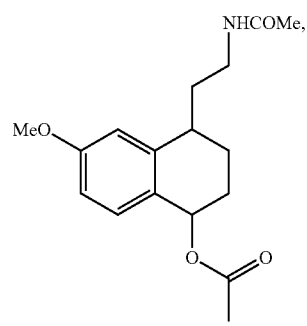

(VII)

which compound of formula (VII) is then hydrolysed and then dehydrated before being subjected to an aromatisation reaction to yield the compound of formula (I), which is isolated in the form of a solid, alternatively, the compound of formula (V) can be subjected to a halogenation reaction to yield the compound of formula (VI"), a particular case of the compounds of formula (VI):

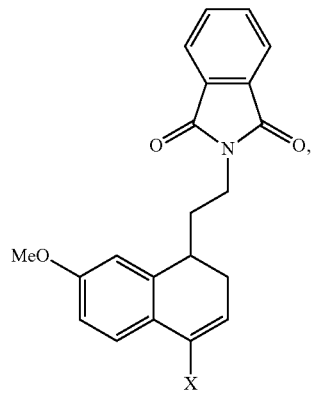

(VI")

wherein X represents a halogen atom (preferably Cl or Br), said compound of formula (VI") then being subjected to an amine-deprotecting reaction and then reacted with acetic anhydride to form the compound of formula (VI$^{ter}$), a particular case of the compounds of formula (VI):

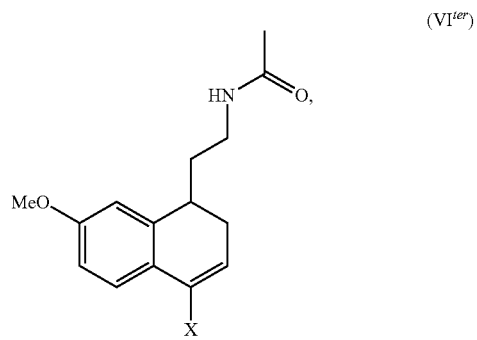

(VI$^{ter}$)

wherein X is as defined hereinbefore, which compound of formula (VI$^{ter}$) is finally aromatised in a basic medium to yield the compound of formula (I), which is isolated in the form of a solid.

In a preferred embodiment of the invention, the amine-deprotecting reaction, when the amine function is protected by a phthalimide group, is carried out in the presence of a reducing agent such as sodium borohydride. Hydrazine-type agents may also be used.

Preferably, the step of aromatisation of the compound of formula (VII) may be carried out using a benzoquinone such as 2,3-dichloro-5,6-dicyano-1,4-benzoquinone (DDQ), whereas aromatisation of the compound of formula (VI$^{ter}$) is advantageously carried out in the presence of a strong non-nucleophilic base. This latter reaction is carried out in a polar protic medium. In a preferred embodiment of the invention, aromatisation of the compound of formula (VI$^{ter}$) is carried out in the presence of an alcoholate/alcohol couple, and even more preferably in the presence of the couple potassium tert-butylate/tert-butanol or the couple potassium 3-methyl-3-pentylate/3-methyl-3-pentanol.

In another variant of the invention, addition of a compound of formula (II) with a compound of formula (III) wherein R' and R" each represent a methyl group is carried out to yield the adduct of formula (IV'):

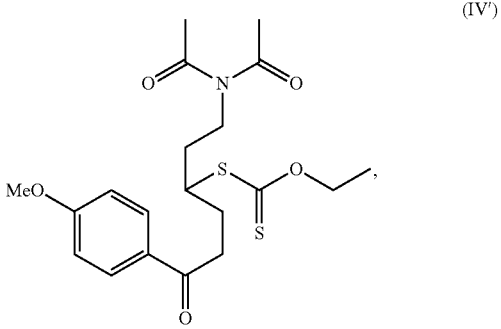 [SMILES: CCOC(=S)SC(CCC(=O)c1ccc(OC)cc1)CCN(C(C)=O)C(C)=O]

(IV')

which is subjected to a deprotection reaction in the presence of a base (such as triethylamine) to yield the compound of formula (IV"), which is optionally isolated:

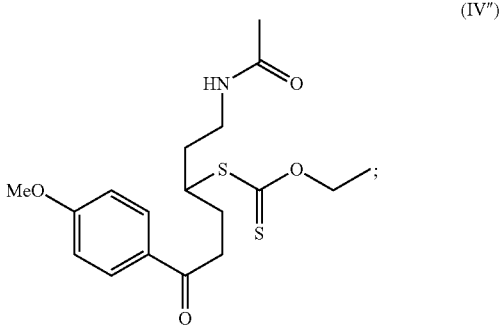 [SMILES: CCOC(=S)SC(CCNC(C)=O)CCC(=O)c1ccc(OC)cc1]

said compound of formula (IV''') is then subjected to a cyclisation reaction in the presence of a free radical initiator to yield the compound of formula (V'), a particular case of the compounds of formula (V):

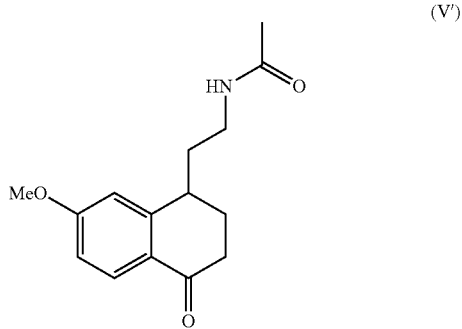 [SMILES: COc1ccc2c(c1)C(CCNC(C)=O)CCC2=O]

which is converted into a vinyl halide and then subjected to an aromatisation reaction to yield the compound of formula (I), which is isolated in the form of a solid.

This process is especially valuable for the following reasons:
  it makes it possible to obtain the compound of formula (I) on an industrial scale in good yields, starting from a simple, low-cost starting material;
  only the intermediate of formulae (V) requires a purification and isolation step.

The compounds of formulae (V), (VI) and (VII) obtained according to the process of the invention are new and useful as intermediates in the synthesis of agomelatine.
  Preferred compounds of formula (V) are as follows:
  2-[2-(7-methoxy-4-oxo-1,2,3,4-tetrahydro-1-naphthyl) ethyl]-1H-isoindole-1,3(2H)-dione,
  N-[2-(7-methoxy-4-oxo-1,2,3,4-tetrahydro-1-naphthyl) ethyl]acetamide.
  Preferred compounds of formula (VI) are as follows:
  2-[2-(4-chloro-7-methoxy-1,2-dihydro-1-naphthyl) ethyl]-1H-isoindole-1,3(2H)-dione,
  2-[2-(4-bromo-7-methoxy-1,2-dihydro-1-naphthyl) ethyl]-1H-isoindole-1,3(2H)-dione,
  N-[2-(4-chloro-7-methoxy-1,2-dihydro-1-naphthyl)ethyl] acetamide,
  N-[2-(4-bromo-7-methoxy-1,2-dihydro-1-naphthyl) ethyl]acetamide,
  N-[2-(7-methoxy-1,2-dihydro-1-naphthyl)ethyl]acetamide.

The Examples hereinbelow illustrate the invention without limiting it in any way.

For the purpose of validating the reaction route, the synthesis intermediates were systematically isolated and characterised. However, it is possible to considerably optimise the procedures by limiting the number of intermediates isolated. Accordingly, Example 5 given hereinbelow corresponds to the same reaction route as that used in Example 4 but with the difference that only N-[2-(7-methoxy-4-oxo-1,2,3,4-tetrahydro-1-naphthyl)-ethyl]acetamide was isolated.

EXAMPLE 1

N-[2-(7-Methoxy-1-naphthyl)ethyl]acetamide

Step A: S-[(1,3-Dioxo-1,3-dihydro-2H-isoindol-2-yl) methyl]-O-ethyl dithiocarbonate To a cold (0° C.) solution of N-(chloromethyl)phthalimide (40.0 g, 205.0 mmol) in acetone (400 mL) there is added, in successive portions, potassium O-ethylxanthate (36.1 g, 225.0 mmol). The reaction mixture is stirred at 0° C. for 30 minutes and then the solvent is evaporated off. The residue thereby obtained is taken up in water. The aqueous phase is extracted with dichloromethane, whilst the organic phases are dried over $MgSO_4$ and concentrated under reduced pressure. The residue thereby obtained is recrystallised from a mixture of ethyl acetate and petroleum ether to yield the title product in a yield of 74%.

$^1$H NMR (δ, ppm) 7.90-7.84 (m, 2H, CH-2), 7.77-7.72 (m, 2H, CH-1), 5.33 (s, 2H, (CDCl$_3$, 400 MHz) CH$_2$-5), 4.68 (q, 2H, J=7.1 Hz, CH$_2$-7), 1.46 (t, 3H, J=7.1 Hz, CH$_3$-8).
$^{13}$C NMR (δ, 210.2 (CS), 166.6 (NCO), 134.4 (CH-1), 131.8 (C-3), 123.6 (CH-2), ppm) (CDCl$_3$, 100 70.5 (CH$_2$-7), 41.2 (CH$_2$-5), 13.7 (CH$_3$-8). MHz)

Step B: S-[1-[2-(1,3-dioxo-1,3-dihydro-2H-isoindol-2-yl)ethyl]-4-(4-methoxyphenyl)-4-oxobutyl]-O-ethyl dithiocarbonate A mixture of 1-(4-methoxyphenyl)-4-penten-1-one[1] (11.0 g, 57.6 mmol) and the xanthate obtained in Step A (19.4 g, 69.2 mmol) in ethyl acetate (580 mL) is heated at reflux under a nitrogen atmosphere for 15 minutes. Then, 10 mol % dilauroyl peroxide are added every 1.5 hours. After adding 4×10 mol % and 1×5 mol % dilauroyl peroxide, the solvent is finally evaporated off and the residue obtained is purified by flash column chromatography (petroleum ether-ethyl acetate: 80-20) to yield the title compound in the form of an oil in a yield of 78%.

[1] 1-(4-Methoxyphenyl)-4-penten-1-one is obtained according to the protocol described in Pattisson, V. A. et al., *J. Am. Chem. Soc.* 1962, 84, 4295.

HRMS (EI, m/z) Calc. for $C_{24}H_{25}NO_5S_2$: 471.1174; found: 471.1172.

Step C: 2-[2-(7-Methoxy-4-oxo-1,2,3,4-tetrahydro-1-naphthyl)ethyl]-1H-isoindole-1,3(2H)-dione A solution of the product obtained in Step B (20.6 g, 43.7 mmol) in chlorobenzene (660 mL) is refluxed under a nitrogen atmosphere for 15 minutes. Then 10 mol % of dilauroyl peroxide are added every 15 minutes until all the starting reagent has been consumed. The mixture is cooled to ambient temperature and concentrated under reduced pressure. Acetonitrile is then introduced to cause a large part of the dilauroyl peroxide compounds to precipitate out. The mixture is then filtered, concentrated under reduced pressure and purified by flash column chromatography (petroleum ether-ethyl acetate: 90-10, then 70-30) to yield the title product in the form of a solid in a yield of 39%.

HRMS (EI, m/z) Calc. for $C_{21}H_{19}NO_4$: 349.1314; found: 349.1316.

Step D: 4-[2-(Acetylamino)ethyl]-6-methoxy-1,2,3,4-tetrahydro-1-naphthyl acetate To a solution of the tetralone obtained in Step C (350 mg, 1.0 mmol) in isopropanol (10 mL) at ambient temperature there is added sodium borohydride (190 mg, 5.0 mmol). The mixture is stirred at reflux overnight and then a solution of sodium hydroxide (80 mg, 2.0 mmol) in water (2.0 mL) is added dropwise. The mixture is maintained under reflux for 30 minutes, and then acetone (1.5 mL) is added. After 10 minutes, the mixture is cooled to ambient temperature before being concentrated under reduced pressure. The oil thereby obtained is dissolved in dichloromethane (10 mL). Dimethylaminopyridine (270 mg, 2.2 mmol) is then added, followed by acetic anhydride (210 µL, 2.2 mmol) dropwise. The solution is stirred at ambient temperature for 1 hour and then water is added. The pH of the solution is adjusted to from 8 to 9 by adding saturated sodium hydrogen carbonate solution. The aqueous phase is extracted with dichloromethane and the organic phases are washed with saturated NaCl solution, dried over magnesium sulphate, filtered and evaporated. The title compound is obtained after purification by flash column chromatography (ethyl acetate-petroleum ether: 90-10, then ethyl acetate-methanol: 90-10) in the form of an oil in a yield of 79%.

HRMS (EI, m/z) Calc. for $C_{17}H_{23}NO_4$: 305.1627; found: 305.1630.

Step E: N-[2-(7-Methoxy-1,2-dihydro-1-naphthyl)ethyl]acetamide

To a solution of the compound obtained in Step D (261 mg, 0.86 mmol) in a mixture of methanol/water (2/0.2 mL) at ambient temperature there is added sodium hydroxide (86 mg, 2.14 mmol). The mixture is stirred for 1 hour under reflux, and the solution is then cooled. Hydrochloric acid (2.6 mL, 2.6 mmol, 1N) is added and the mixture is stirred overnight. The aqueous phase is extracted with dichloromethane, and the organic phases are washed with saturated NaCl solution, dried over magnesium sulphate, filtered and evaporated. The title compound is obtained after purification by flash column chromatography (ethyl acetate-petroleum ether: 90-10, then ethyl acetate-methanol: 90-10) in the form of an oil in a yield of 61%.

HRMS (EI, m/z) Calc. for $C_{15}H_{19}NO_2$: 245.1416; found: 245.1413.

Step F: N-[2-(7-Methoxy-1-naphthyl)ethyl]acetamide

To a solution of the compound obtained in Step E (100 mg, 0.41 mmol) in dichloromethane (4 mL) there is added, at ambient temperature, DDQ (111 mg, 0.49 mmol). The reaction mixture is stirred for 2 days and then washed with saturated $NaHCO_3$ solution. The aqueous phase is extracted with ethyl acetate, and the organic phases are collected and then dried using brine and then over $MgSO_4$. After filtration, the solvents are evaporated off under reduced pressure and the crude reaction mixture obtained is purified by chromatography on a silica column (eluant: ethyl acetate/petroleum ether 90/10, then ethyl acetate/methanol 90/10) to yield the title product in a yield of 48%.

EXAMPLE 2

N-[2-(7-Methoxy-1-naphthyl)ethyl]acetamide

Step A: 2-[2-(7-Methoxy-4-oxo-1,2,3,4-tetrahydro-1-naphthyl)ethyl]-1H-isoindole-1,3(2H)-dione The compound is obtained using the procedures described in Steps A to C of Example 1.

Step B: 2-[2-(4-Chloro-7-methoxy-1,2-dihydro-1-naphthyl)ethyl]-1H-isoindole-1,3(2H)-dione To a solution of DMF (190 µL, 2.4 mmol) in 1.0 mL of dichloromethane at 0° C. there is added $POCl_3$ (190 mL, 2.0 mmol)[2] dropwise. After 30 minutes, the tetralone obtained in Step A (0.70 g, 2.0 mmol), dissolved in dichloromethane (2.0 mL), is added dropwise to the Vilsmeier reagent. The temperature of the reaction mixture is allowed to return to ambient temperature. The mixture is stirred until the reagents have completely disappeared (monitored by TLC). Saturated sodium acetate solution is then added, and then the solution is extracted with dichloromethane. The organic phase is washed with saturated NaCl solution and with water, and is then dried over $MgSO_4$, filtered and evaporated. The title compound is obtained by flash column chromatography (petroleum ether-ethyl acetate: 80-20) in the form of a solid in a yield of 75%.

[2]Lilienkampf A. et al., *Org. Letters*. 2003, 5, 3387

HRMS (EI, m/z) Calc. for $C_{21}H_{18}ClNO_3$: 367.0975; found: 367.0975.

Step C: N-[2-(4-Chloro-7-methoxy-1,2-dihydro-1-naphthyl)ethyl]acetamide

To a solution of the compound obtained in Step B (370 mg, 1.0 mmol) in isopropanol (10 mL) at ambient temperature there is added sodium borohydride (190 mg, 5.0 mmol). The mixture is stirred for 3 hours under reflux, and then a solution of sodium hydroxide (80 mg, 2.0 mmol) in water (2.0 mL) is added dropwise. The mixture is maintained under reflux for 30 minutes, and then acetone (1.5 mL) is added. After 10 minutes, the mixture is cooled to ambient temperature before being concentrated under reduced pressure. The oil thereby obtained is dissolved in dichloromethane (10 mL). Dimethylaminopyridine (270 mg, 2.2 mmol) is then added, followed by acetic anhydride (210 µL, 2.2 mmol) dropwise. The solution is stirred at ambient temperature for 1 hour and then water is added. A few drops of hydrochloric acid (1N) are also added to obtain an acid pH. The aqueous phase is extracted with dichloromethane and the organic phases are washed with saturated NaCl solution, dried over magnesium sulphate, filtered and evaporated. The title compound is obtained after purification by flash column chromatography (ethyl acetate-petroleum ether: 90-10, then ethyl acetate-methanol: 90-10) in the form of an oil in a yield of 71%.

HRMS (EI, m/z) Calc. for $C_{15}H_{18}ClNO_2$: 279.1026; found: 279.1030.

Step D: N-[2-(7-Methoxy-1-naphthyl)ethyl]acetamide

To a solution of the compound obtained in Step C (125 mg, 0.45 mmol) in tert-butanol (1 mL) at reflux there is added potassium tert-butylate (200 mg, 1.8 mmol). The mixture is stirred for 3 hours under reflux and then hydrochloric acid (1N) is added. The aqueous phase is extracted with dichloromethane and the organic phases are washed with saturated NaCl solution, dried over magnesium sulphate, filtered and evaporated. The title compound is obtained after purification by flash column chromatography (ethyl acetate-petroleum ether: 90-10, then ethyl acetate-methanol: 90-10) in the form of a solid in a yield of 68%.

HRMS (EI, m/z) Calc. for $C_{15}H_{19}NO_3$: 261.1365; found: 261.1369.

EXAMPLE 3

N-[2-(7-Methoxy-1-naphthyl)ethyl]acetamide

Step A: 2-[2-(7-Methoxy-4-oxo-1,2,3,4-tetrahydro-1-naphthyl)ethyl]-1H-isoindole-1,3(2H)-dione The compound is obtained using the procedures described in Steps A to C of Example 1.

Step B: 2-[2-(4-Bromo-7-methoxy-1,2-dihydro-1-naphthyl)ethyl]-1H-isoindole-1,3(2H)-dione To a cold solution of triphenyl phosphite (290 µL, 1.1 mmol) in dichloromethane (3.5 mL), maintained at −78° C. under a nitrogen atmosphere, bromine (60 µL, 1.2 mmol) is added dropwise[3]. Triethylamine (180 µL, 1.3 mmol) and the tetralone obtained in Step A (350 mg, 1.0 mmol) are added to the solution. The reaction mixture is stirred for 18 hours whilst its temperature is brought back to ambient temperature. The mixture is then heated at reflux for one hour before being concentrated and purified by flash column chromatography (petroleum ether-ethyl acetate: 80-20). The title compound is obtained in the form of an oil in a yield of 95%.

[3]Spaggiari A. et al., *J. Org. Chem.* 2007, 72, 2216

HRMS (EI, m/z) Calc. for $C_{21}H_{18}BrNO_3$: 411.0470; found: 411.0470.

Step C: N-[2-(4-Bromo-7-methoxy-1,2-dihydro-1-naphthyl)ethyl]acetamide

To a solution of the compound obtained in Step B (390 mg, 0.95 mmol) in isopropanol (10 mL) at ambient temperature there is added sodium borohydride (179 mg, 4.7 mmol). The mixture is stirred for 3 hours under reflux, and then a solution of sodium hydroxide (76 mg, 1.9 mmol) in water (2.0 mL) is added dropwise. The mixture is maintained under reflux for 30 minutes, and then acetone (1.5 mL) is added. After 10 minutes, the mixture is cooled to ambient temperature before being concentrated under reduced pressure. The oil thereby obtained is dissolved in dichloromethane (10 mL). Dimethylaminopyridine (255 mg, 2.1 mmol) is then added, followed by acetic anhydride (200 µL, 2.1 mmol) dropwise. The solution is stirred at ambient temperature for 1 hour and then water is added. A few drops of hydrochloric acid (1N) are also added to obtain an acid pH. The aqueous phase is extracted with dichloromethane and the organic phases are washed with saturated NaCl solution, dried over magnesium sulphate, filtered and evaporated. The title compound is obtained after purification by flash column chromatography (ethyl acetate-petroleum ether: 90-10, then ethyl acetate-methanol: 90-10) in the form of an oil in a yield of 64%.

HRMS (EI, m/z) Calc. for $C_{15}H_{18}BrNO_2$: 323.0521; found: 323.0517.

Step D:
N-[2-(7-Methoxy-1-naphthyl)ethyl]acetamide

The compound is obtained using the procedure described in Step D of Example 2.

EXAMPLE 4

N-[2-(7-ethoxy-1-naphthyl)ethyl]acetamide

Step A: S-[(Acetylamino)methyl]-O-ethyl dithiocarbonate

Acetamide (29.5 g, 0.50 mol) and paraformaldehyde (18.0 g, 0.6 mol) are dissolved in acetic anhydride (250 mL) and acetic acid (50 mL). The solution is heated at 80° C. for 5 hours, cooled and evaporated. 20% by weight of the resulting oil is then dissolved in ethanol (200 mL) and cooled to 0° C. before adding potassium O-ethylxanthate (19.2 g, 0.12 mol). The reaction mixture is stirred at ambient temperature for 6 hours, and then water is added and a large part of the ethanol is removed from the mixture under reduced pressure. The suspension is held at 0° C. for 20 minutes and filtered. After dissolving the residue in dichloromethane, the organic phase is dried over magnesium sulphate, filtered and evaporated to yield the title compound in the form of a solid in a yield of 57%.

HRMS (EI, m/z) Calc. for $C_6H_{11}NO_2S_2$: 193.0231; found: 193.0230.

Step B: S-[(Diacetylamino)methyl]-O-ethyl dithiocarbonate

A solution of the xanthate obtained in Step A (5.93 g, 30.7 mmol) in isoprenyl acetate (45 mL) is refluxed overnight in the presence of a few crystals of p-toluenesulphonic acid and is then cooled and concentrated under reduced pressure. The title compound is obtained in the form of an oil after purification by flash column chromatography (ethyl acetate-petroleum ether: 80-20) in a quantitative yield.

HRMS (EI, m/z) Calc. for $C_8H_{13}NO_3S_2$: 235.0337; found: 235.0338.

Step C: S-[1-[2-(Diacetylamino)ethyl]-4-(4-methoxyphenyl)-4-oxobutyl]-O-ethyl dithiocarbonate The compound of Step B is used directly without having been purified. The oil obtained in the Step above (25% by weight) is added to a solution of 1-(4-methoxyphenyl)-4-penten-1-one (2.92 g, 15.3 mmol) in ethyl acetate (8 mL) and refluxed under a nitrogen atmosphere for 15 minutes. 10 mol % dilauroyl peroxide (305 mg) are then added every 1.5 hours. After adding 2×10 mol % and 1×5 mol % dilauroyl peroxide, the solvent is evaporated off. The title compound is obtained after purification by flash column chromatography (ethyl acetate-petroleum ether: 90-10, then pure ethyl acetate) in the form of an oil in a yield of 72%.

HRMS (EI, m/z) Calc. for $C_{20}H_{27}NO_5S_2$: 425.1331; found: 425.1331.

Step D: N-[2-(7-methoxy-4-oxo-1,2,3,4-tetrahydro-1-naphthyl)ethyl]acetamide

A solution of the compound obtained in Step C (1.10 g, 2.59 mmol) in ethyl acetate (52 mL) is refluxed under a nitrogen atmosphere for 15 minutes, and then dibenzoyl peroxide (940 mg, 3.88 mmol) and 20 mol % dilauroyl peroxide (206 mg) are added every 1.5 hours until the reagent has completely disappeared. The mixture is then cooled to ambient temperature and concentrated under reduced pressure. The oil thereby obtained is dissolved in methanol (5 mL) in the presence of triethylamine (3.6 mL) and then refluxed for 1 hour. The mixture is concentrated under reduced pressure and purified by flash column chromatography (ethyl acetate-petroleum ether: 90-10, then ethyl acetate-methanol: 80-20) to yield the title compound in the form of an oil in a yield of 56%.

HRMS (EI, m/z) Calc. for $C_{15}H_{19}NO_3$: 261.1365; found: 261.1369.

Step E:
N-[2-(7-Methoxy-1-naphthyl)ethyl]acetamide

To a solution of DMF (93 µL, 1.2 mmol) in 0.5 mL of dichloromethane at 0° C. there is added $POCl_3$ (92 mL, 1.0 mmol) dropwise. After 30 minutes, the tetralone obtained in Step D (261 mg, 1.0 mmol), dissolved in dichloromethane (1 mL), is added dropwise to the Vilsmeier reagent. The reaction mixture is allowed to return to ambient temperature, being stirred overnight. Saturated sodium acetate (NaOAc) solution is then added and the solution is then extracted with dichloromethane. The organic phase is washed using saturated NaCl solution and water and is then dried over $MgSO_4$, filtered and evaporated.

The residue is dissolved in tert-butanol (2 mL) and refluxed. Potassium tert-butylate (450 mg, 4.0 mmol) is added, and the mixture is maintained under reflux for 3 hours. After cooling to ambient temperature, hydrochloric acid (1N) is added. The aqueous phase is extracted with dichloromethane, and the organic phase is washed with saturated NaCl solution and then dried over $MgSO_4$, filtered and evaporated. The title compound is obtained after purification by flash column chromatography (ethyl acetate-petroleum ether: 90-10, then ethyl acetate-methanol: 90-10) in the form of a solid in a yield of 53%.

HRMS (EI, m/z) Calc. for $C_{15}H_{19}NO_3$: 261.1365; found: 261.1369.

EXAMPLE 5

N-[2-(7-Methoxy-1-naphthyl)ethyl]acetamide

Step A: S-[(Acetylamino)methyl]-O-ethyl dithiocarbonate

The title compound is obtained according to the experimental protocol described in Example 4.

Step B: N-[2-(7-methoxy-4-oxo-1,2,3,4-tetrahydro-1-naphthyl)ethyl]acetamide

A solution of the xanthate obtained in Step A (9.34 g, 48.3 mmol) in isoprenyl acetate (75 mL) is refluxed for 3 hours in the presence of a few crystals of p-toluenesulphonic acid and is then evaporated to yield S-[(diacetylamino)methyl]-O-ethyl dithiocarbonate. A sample of the crude product thereby obtained (1.0 g) is added to a solution of 1-(4-methoxyphenyl)-4-penten-1-one (800 mg, 4.20 mmol) in ethyl acetate (4 mL) and refluxed under a nitrogen atmosphere for 15 minutes. 10 mol % dilauroyl peroxide (170 mg) are then added every 1.5 hours. After adding 4×10 mol % and 1×5 mol % dilauroyl peroxide, the solvent is evaporated off to yield S-[1-[2-(diacetylamino)ethyl]-4-(4-methoxyphenyl)-4-oxobutyl]-O-ethyl dithiocarbonate. The crude product thereby obtained is dissolved in ethyl acetate (85 mL). The solution is refluxed under a nitrogen atmosphere for 15 minutes, and then dibenzoyl peroxide (1.53 g, 6.30 mmol) and 20 mol % dilauroyl peroxide (335 mg) are added every 1.5 hours until the reagent has completely disappeared. The mixture is then cooled to ambient temperature and concentrated under reduced pressure. The oil thereby obtained is dissolved in methanol (8.5 mL) in the presence of triethylamine (5.9 mL) and then refluxed for 1 hour. The mixture is concentrated under reduced pressure and purified by flash column chromatography (ethyl acetate-petroleum ether: 90-10, then ethyl acetate-methanol: 80-20) to yield the title compound in the form of an oil in a yield of 44%.

HRMS (EI, m/z) Calc. for $C_{15}H_{19}NO_3$: 261.1365; found: 261.1369.

Step C:
N-[2-(7-Methoxy-1-naphthyl)ethyl]acetamide

The title compound is obtained according to the protocol described in Step E of Example 4.

HRMS (EI, m/z) Calc. for $C_{15}H_{19}NO_3$: 261.1365; found: 261.1369.

The invention claimed is:
1. A process for the synthesis of a compound of formula (I):

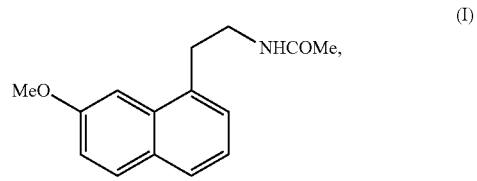

wherein 1-(4-methoxyphenyl)-4-penten-1-one of formula (II):

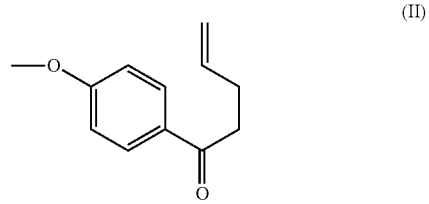

is reacted, in the presence of a free radical initiator, with a compound of formula (III):

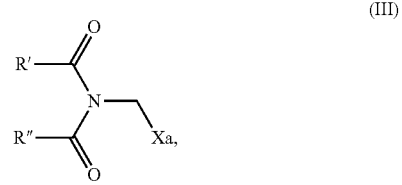

wherein R' and R", which may be the same or different, each represent a linear or branched $(C_1-C_6)$alkyl group or R' and R" together form a $(C_2-C_3)$alkylene chain, it being possible for the ring thereby formed to be fused with a phenyl group, and Xa represents a group —S—C (S)—OR wherein R represents a linear or branched ($C_1$-$C_6$)alkyl group, to yield the adduct of formula (IV):

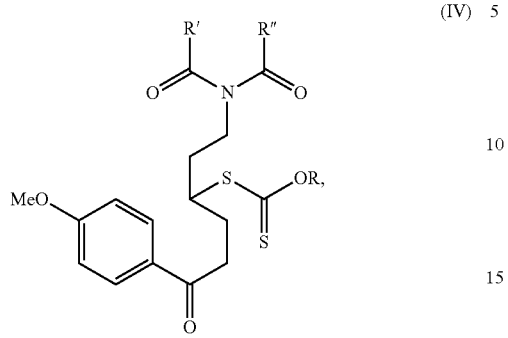
(IV)

wherein R, R' and R" are as defined hereinbefore,
wherein the compound of formula (IV) is optionally isolated,
the amine function of which may optionally be deprotected and converted into an acetamide function,
which compound of formula (IV) is subjected to a cyclisation reaction in the presence of a free radical initiator to form the compound of formula (V):

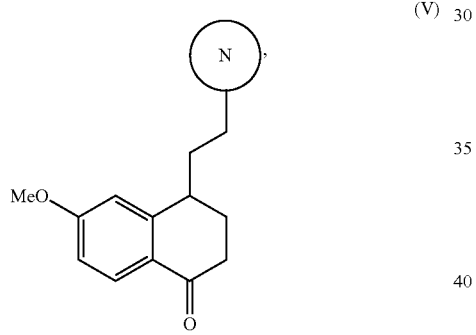
(V)

wherein the group

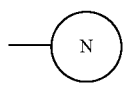

represents a protected amine function defined as follows:

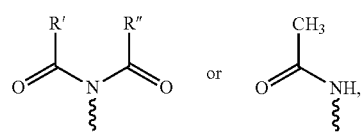

wherein R' and R" are as defined hereinbefore,
the amine function of which compound of formula (V) may optionally be deprotected, wherein the compound of formula (V) is either subjected to reduction-esterification followed by dehydration or converted into a vinyl halide to yield the compound of formula (VI):

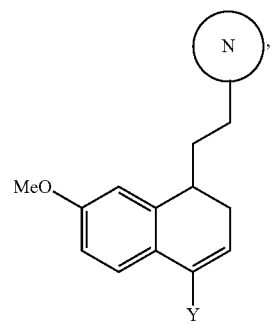
(VI)

wherein Y represents a halogen atom or a hydrogen atom, and the group

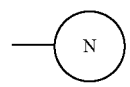

is as defined hereinbefore,
the protected amine function of which compound of formula (VI) is converted into an acetamide function where applicable, i.e. when that conversion has not been carried out earlier, to yield the compound of formula (VI'):

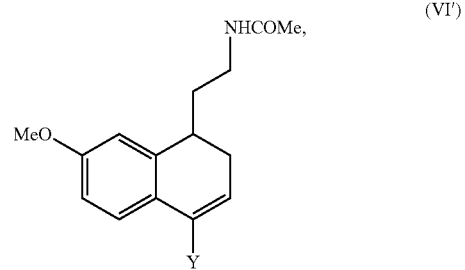
(VI')

wherein Y is as defined hereinbefore,
which compound of formula (VI') is subjected to an aromatisation reaction to yield the compound of formula (I), which is isolated in the form of a solid.

2. The process according to claim 1, wherein the compound of formula (III) is selected from:

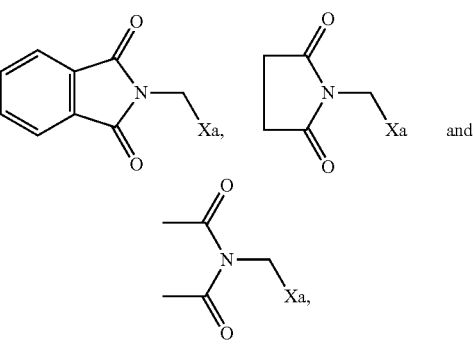
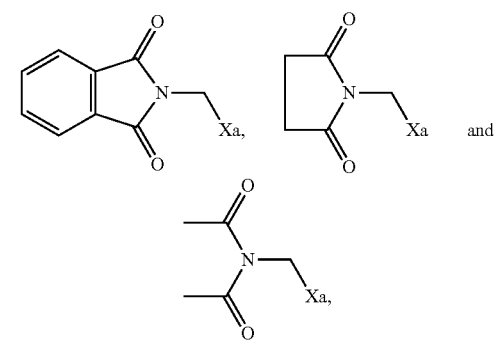

wherein Xa represents —S—C(S)—OR wherein R represents a linear or branched ($C_1$-$C_6$)alkyl group.

3. The process according to claim 1, wherein the group Xa represents —S—C(S)—OC$_2$H$_5$.

4. The process according to claim 1, wherein the free radical reactions are initiated by thermal means at a temperature of from 50 to 140° C.

5. The process according to claim 1, wherein the step of addition of the compound of formula (II) to the compound of formula (III) is initiated in the presence of dilauroyl peroxide.

6. The process according to claim 1, wherein the reaction of cyclisation of the adduct of formula (IV) is carried out in the presence of dilauroyl peroxide optionally with dibenzoyl peroxide.

7. The process according to claim 1, wherein the step of addition of the compound of formula (II) to the compound of formula (III) and the step of cyclisation of the adduct of formula (IV) are carried out in ethyl acetate.

8. The process according to claim 1, wherein the compound of formula (V) wherein R' and R" together form an ethylene chain, the ring thereby formed being fused to a phenyl group, is subjected to an amine-deprotecting reaction and is then reacted with acetic anhydride to form the compound of formula (VII):

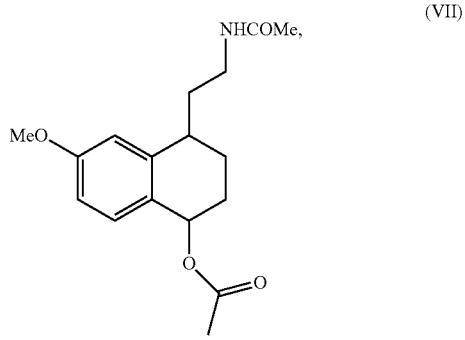

(VII)

which compound of formula (VII) is then hydroloysed and then dehydrated before being subjected to an aromatisation reaction to yield the compound of formula (I), which is isolated in the form of a solid.

9. The process according to claim 1, wherein the compound of formula (V) wherein R' and R" together form an ethylene chain, the ring thereby formed being fused to a phenyl group, is subjected to a halogenation reaction to yield the compound of formula (VI"):

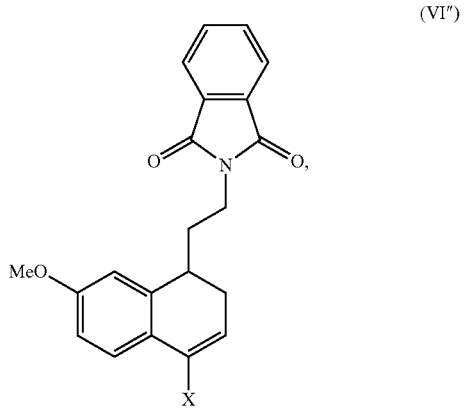

(VI")

wherein X represents a halogen atom,
which compound of formula (VI") is subjected to an amine-deprotecting reaction and then reacted with acetic anhydride to form the compound of formula (VI$^{ter}$):

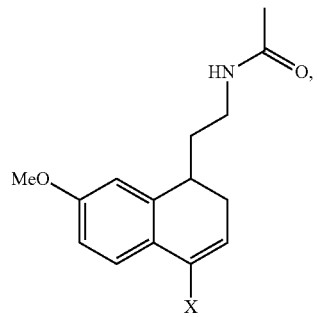

(VI$^{ter}$)

wherein X is as defined hereinbefore,
which compound of formula (VI$^{ter}$) is aromatised in a basic medium to yield the compound of formula (I), which is isolated in the form of a solid.

10. The process according to claim 9, wherein X represents Cl.

11. The process according to claim 9, wherein X represents Br.

12. The process according to claim 1, wherein the reaction deprotecting the amine function of the compound of formula (V), when the amine function is protected by a phthalimide group, is carried out in the presence of sodium borohydride or a hydrazine-type agent.

13. The process according to claim 8, wherein the step of aromatisation of the compound of formula (VII) is carried out using a benzoquinone.

14. The process according to claim 13, wherein the benzoquinone is 2,3-dichloro-5,6-dicyano-1,4-benzoquinone (DDQ).

15. The process according to claim 9, wherein the aromatisation of the compound of formula (VI$^{ter}$) is carried out in the presence of a strong non-nucleophilic base.

16. The process according to claim 9, wherein the aromatisation of the compound of formula (VI$^{ter}$) is carried out in the presence of an alcoholate/alcohol couple.

17. The process according to claim 16, wherein the aromatisation of the compound of formula (VI$^{ter}$) is carried out in the presence of the couple potassium tert-butylate/tert-butanol or the couple potassium 3-methyl-3-pentylate/3-methyl-3-pentanol.

18. The process according to claim 1, wherein the addition of the compound of formula (II) with the compound of formula (III) wherein R' and R" each represent a methyl group is carried out to yield the adduct of formula (IV'):

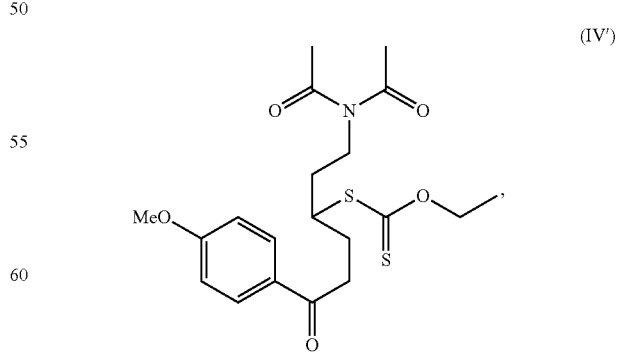

(IV')

which is subjected to a deprotection reaction in the presence of a base to yield the compound of formula (IV"), which is optionally isolated:

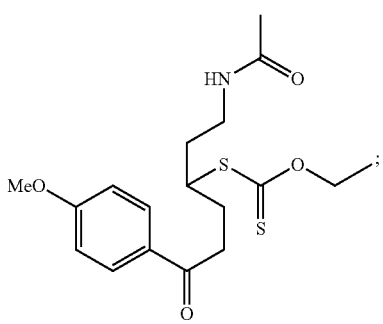

which compound of formula (IV″) is then subjected to a cyclisation reaction in the presence of a free radical initiator to yield the compound of formula (V′):

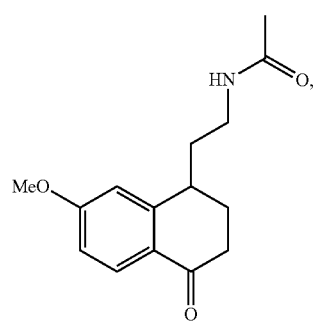

which compound of formula (V′) is converted into a vinyl halide and then subjected to an aromatisation reaction to yield the compound of formula (I), which is isolated in the form of a solid.

19. The process according to claim 18, wherein the base is triethylamine.

20. A process for the synthesis of agomelatine starting from the compound of formula (V):

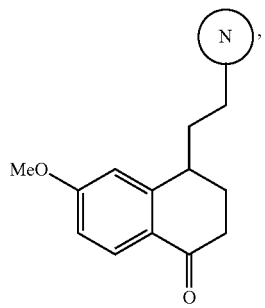

wherein the group

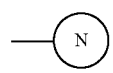

represents a protected amine function defined as follows:

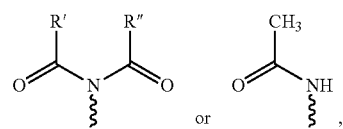

wherein R' and R", which may be the same or different, each represent a linear or branched $(C_1-C_6)$alkyl group or R' and R" together form a $(C_2-C_3)$alkylene chain, it being possible for the ring thereby formed to be fused with a phenyl group, wherein the compound of formula (V) is obtained according to the synthesis process according to claim 1.

21. A process for the synthesis of agomelatine starting from the compound of formula (VI):

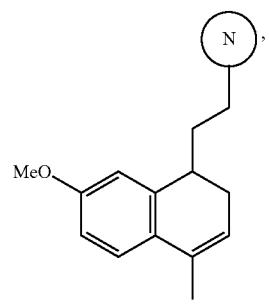

wherein Y represents a halogen atom or a hydrogen atom, and the group

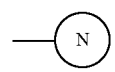

represents a protected amine function defined as follows:

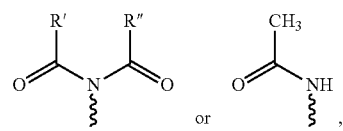

wherein R' and R", which may be the same or different, each represent a linear or branched $(C_1-C_6)$alkyl group or R' and R" together form a $(C_2-C_3)$alkylene chain, it being possible for the ring thereby formed to be fused with a phenyl group, wherein the compound of formula (VI) is obtained according to the synthesis process according to claim 1.

22. A process for the synthesis of agomelatine starting from the compound of formula (VII):

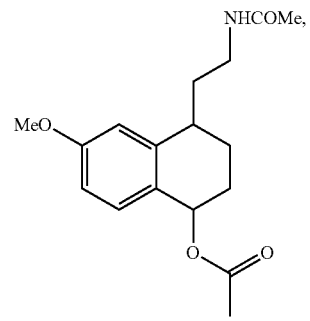

wherein the compound of formula (VII) is obtained according to the synthesis process according to claim 8.

23. A compound of formula (V):

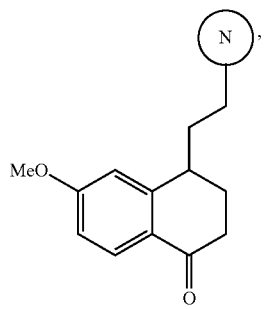
(V)

wherein the group

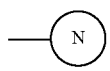

represents a protected amine function defined as follows:

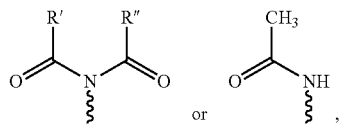

wherein R' and R", which may be the same or different, each represent a linear or branched $(C_1-C_6)$alkyl group or R' and R" together form a $(C_2-C_3)$alkylene chain, it being possible for the ring thereby formed to be fused with a phenyl group.

24. The compound according to claim 23, which is selected from the following compounds:

2-[2-(7-methoxy-4-oxo-1,2,3,4-tetrahydro-1-naphthyl)ethyl]-1H-isoindole-1,3(2H)-dione and N-[2-(7-methoxy-4-oxo-1,2,3,4-tetrahydro-1-naphthyl)ethyl]acetamide.

25. A compound of formula (VI):

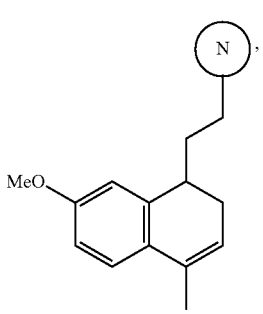
(VI)

wherein Y represents a halogen atom or a hydrogen atom, and the group

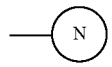

represents a protected amine function defined as follows:

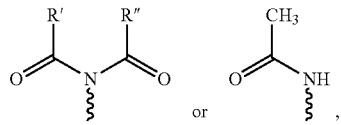

wherein R' and R", which may be the same or different, each represent a linear or branched $(C_1-C_6)$alkyl group or R' and R" together form a $(C_2-C_3)$alkylene chain, it being possible for the ring thereby formed to be fused with a phenyl group.

26. The compound according to claim 25, which is selected from the following compounds:

2-[2-(4-chloro-7-methoxy-1,2-dihydro-1-naphthyl)ethyl]-1H-isoindole-1,3(2H)-dione, 2-[2-(4-bromo-7-methoxy-1,2-dihydro-1-naphthyl)ethyl]-1H-isoindole-1,3(2H)-dione, N-[2-(4-chloro-7-methoxy-1,2-dihydro-1-naphthyl)ethyl]acetamide, N-[2-(4-bromo-7-methoxy-1,2-dihydro-1-naphthyl)ethyl]acetamide, and N-[2-(7-methoxy-1,2-dihydro-1-naphthyl)ethyl]acetamide.

27. A compound of formula (VII):

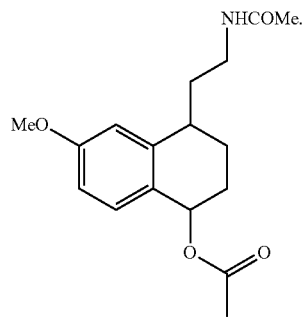
(VII)

* * * * *

UNITED STATES PATENT AND TRADEMARK OFFICE
CERTIFICATE OF CORRECTION

PATENT NO. : 8,871,975 B2  Page 1 of 1
APPLICATION NO. : 13/977796
DATED : October 28, 2014
INVENTOR(S) : Samir Zard, Béatrice Sire and Mehdi Boumediene It is certified that error appears in the above-identified patent and that said Letters Patent is hereby corrected as shown below:

Title Page, item [73] Assignee: "Les Laboratories Servier" should be -- Les Laboratoires Servier --.

Signed and Sealed this
Twelfth Day of May, 2015

Michelle K. Lee
*Director of the United States Patent and Trademark Office*